United States Patent
Lange et al.

(10) Patent No.: US 6,559,334 B1
(45) Date of Patent: May 6, 2003

(54) POLYMERS CHROMATOGRAPHIC SEPARATION OF ENANTIOMERS

(75) Inventors: Walter Lange, Cologne (DE); Michael Grosse-Bley, Cologne (DE); Bruno Bömer, Bergisch Gladbach (DE); Rolf Grosser, Leverkusen (DE); Franz-Peter Hoever, Cologne (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/290,047

(22) Filed: Aug. 12, 1994

Related U.S. Application Data

(63) Continuation of application No. 08/108,369, filed on Aug. 18, 1993, now abandoned.

(30) Foreign Application Priority Data

Aug. 25, 1992 (DE) .......................................... 42 28 135

(51) Int. Cl.$^7$ ............................................ C07C 321/00
(52) U.S. Cl. ........................... 560/16; 548/495; 560/41; 560/125; 560/145; 560/153; 560/169; 564/153
(58) Field of Search ................................ 560/169, 153, 560/41, 145, 16, 125; 548/495; 561/163, 153

(56) References Cited

U.S. PATENT DOCUMENTS

| 4,882,048 A | 11/1989 | Blaschke et al. |
| 4,914,159 A | 4/1990 | Bomer et al. |
| 4,937,000 A | 6/1990 | Bomer et al. |

FOREIGN PATENT DOCUMENTS

| EP | 0379917 | 8/1990 |
| EP | 0464488 | 1/1992 |

OTHER PUBLICATIONS

*Die Makromolekulare Chemie*, Band 178, Nr. 8, Aug. 1977, pp. 2169–2183; "Reactive Copolymers of N–(2–Hydroxyproply)methacrylamide with . . . ", J. Kopecek.

*Chemical Abstracts*, vol. 92, Apr. 28, 1980, No. 17, pp. 1 and 229; 142561g, "The Design of New Synthetic Carriers for Affinity Chromatography", E. Brown et al.

G. Gubitz, "Separation of Drug . . . Selective Review", Chromatographia, vol. 30, No. 9/10, Nov. 1990, pp. 555–564.

*Primary Examiner*—Michael L. Shippen
(74) *Attorney, Agent, or Firm*—Norris McLaughlin & Marcus

(57) ABSTRACT

The invention relates to novel optically active polymerizable dipeptides, to the process for the preparation thereof, to the polymerization thereof and to the use of the polymers as adsorbents for the chromatographic separation of enantiomers.

6 Claims, No Drawings

POLYMERS CHROMATOGRAPHIC SEPARATION OF ENANTIOMERS

This application is a continuation, of application, Ser. No. 08/108,369, filed Aug. 18, 1993 now abandoned.

The invention relates to novel optically active polymerisable dipeptides, to the process for the preparation thereof, to the polymerisation thereof and to the use of the polymers as adsorbents for the chromatographic separation of enantiomers.

The separation of enantiomers of active substances represents an important task because the individual enantiomers often have different biological effects and side effects. The fractionation can advantageously take place by chromatography on chiral stationary phases or adsorbents.

A number of adsorbents suitable for the chromatographic separation of enantiomers of active substances have already been disclosed (G. Gübitz, Chromatographia 30 (1990), 555–564; EP 249 078; EP 379 917). Nevertheless it is repeatedly found that the fractionation of an active substance racemate is impossible or only poor on the known adsorbents.

It has been found, surprisingly, that for a number of active substance racemates the novel adsorbents according to the invention have a very high selectivity which makes fractionation distinctly more efficient than on adsorbents hitherto disclosed. This means that either higher space-time yields are possible in preparative separations, or an improved analysis of enantiomers, for example of biological analytes, is possible.

The invention therefore relates to polymerisable optically active dipeptides of the formula (I)

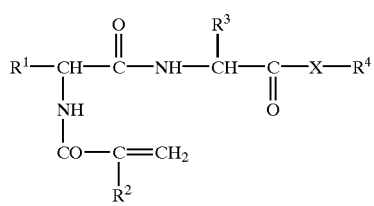

in which
- $R^1$ and $R^3$ are identical or different and represent $C_1$–$C_5$-alkyl, A—O—$CH_2$, A—S—$CH_2$, $CH_3$—S—$(CH_2)_2$, cyclohexyl-$CH_2$, cyclohexyl, phenyl, benzyl, 4-A—O-benzyl, benzyl-$(CH_2)$, indolyl, naphthyl-$CH_2$ or naphthyl, where A is hydrogen, methyl, t-butyl or benzyl,
- $R^2$ denotes hydrogen, methyl or fluorine,
- X represents oxygen or $NR^5$,
  - where $R^5$ is hydrogen, methyl, ethyl or, together with $R^4$, forms a $C_5$–$C_6$-cycloalkyl radical, and
- $R^4$ represents a straight-chain or branched $C_3$–$C_{18}$-alkyl radical or a mono- to tetra-$C_1$–$C_4$-alkyl-substituted $C_3$–$C_{12}$-cycloalkyl radical, benzyl, 1-phenylethyl or represents a phenyl which is mono- to disubstituted by fluorine, chlorine, trifluoromethyl, methoxy or $C_1$–$C_4$-alkyl.

Preferred compounds of the formula (I) are those in which $R^1$, $R^3$ and $R^5$ have the stated meaning, $R^2$ denotes hydrogen or methyl, and $R^4$ represents $C_3$–$C_8$-alkyl (such as, for example, 2-propyl, 3-pentyl, t-butyl, neopentyl), $C_5$–$C_7$-cycloalkyl (cyclopentyl, cyclohexyl, cycloheptyl), up to tetra-$C_1$–$C_4$-alkyl-substituted $C_6$-cycloalkyl (such as menthyl, bornyl, fenchyl), benzyl, 1-phenylethyl, phenyl, 4-t-butylphenyl, 3,5-dichlorophenyl or 3,5-dimethylphenyl.

If X denotes not O but $NR^5$, it is then possible for $R^4$ also to represent methyl and ethyl or to form with $R^5$ a $C_5$–$C_6$ ring.

If $R^4$ is a chiral radical, it is advantageously used in optically active form.

Particularly preferred dipeptides of the formula (I) are those derived from the amino acids alanine, aminobutyric acid, valine, norvaline, leucine, isoleucine, terleucine, norleucine, neopentylglycine, serine, cysteine, methionine, hexahydrophenylalanine, hexahydrophenylglycine, phenylglycine, phenylalanine, tyrosine, homophenylalanine, tryptophan, naphthylalanine or naphthylglycine.

Examples of particularly preferred compounds which may be mentioned are:

N-methacryloyl-S-Leu-S-Ile O-t-butyl ester, N-methacryloyl-S-Leu-S-Phe-d-menthylester, N-methacryloyl-S-Leu-S-Leu-3-pentylamide, N-methacryloyl-S-Val-S-Val-t-butylamide, N-acryloyl-S-Phe-S-Phe-2-propylester, N-methacryloyl-S-Val-S-Ala-1-bornylester, N-methacryloyl-S-Ala-S-Met-3-pentylamide, N-methacryloyl-R-Phg-S-Val-t-butylester, N-methacryloyl-S-Leu-R-Phe-1-menthylester, N-methacryloyl-S-Ala-R-(S)-methyl-Cys-diethylamide, N-methacryloyl-S-Ala-S-Leu-d-menthylester, N-methacryloyl-S-Phg-S-Val-t-butyl ester, N-methacryloyl-S-Leu-S-Ile-3-pentylester, N-methacryloyl-S-Phg-S-Met-diethylamide, N-methacryloyl-S-Leu-R-hexahydrophenylglycine diethylamide, N-methacryloyl-S-Nle-S-Ile-t-butylester.

The compounds of the formula (I) according to the invention are prepared by

A) linking dipeptide derivatives of the formula (II)

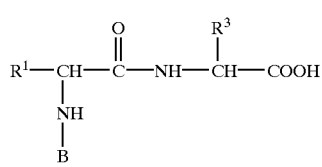

in which
- $R^1$ and $R^3$ have the abovementioned meaning, and
- B represents a group which is customary in peptide chemistry and is easy to eliminate,
  - using the linkage reactions customary in peptide chemistry to the radical $XR^4$
    - where X and $R^4$ have the abovementioned meaning, and subsequently eliminating the radical B using methods customary in peptide chemistry, and reacting the compounds, which are then obtained, of the general formula (III)

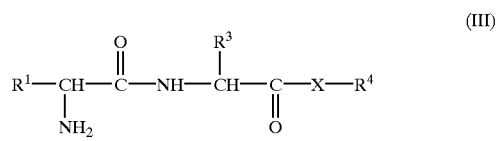

where appropriate in the form of their acid addition products, with acryloyl derivatives of the formula (IV)

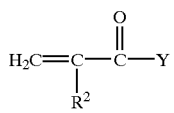

in which
R² has the abovementioned meaning, and
Y represents fluorine, chlorine, bromine or represents the radical —OCO—CR²=CH₂,
in the presence of an acid-binding agent in inert organic solvents to give compounds of the formula (I), or B) linking amino acid derivatives of the formula (V)

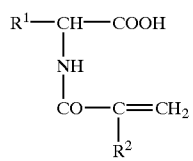

in which
R¹ and R² have the abovementioned meaning,
to a second amino acid derivative of the formula (VI),

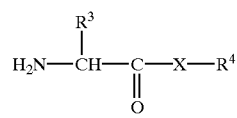

in which
R³, Y and R⁴ have the abovementioned meaning, by customary methods to give dipeptides of the formula (I).

Preferred embodiments of process variant A comprise the use of compounds of the formula (II) in which B represents groups which are easy to eliminate such as t-butoxycarbonyl (BOC) or carbobenzoxycarbonyl (CBZ).

The introduction of the radical XR⁴ represents a linkage reaction which is customary in peptide chemistry. For example, amines react either after activation of the carboxylic acid functionality with bases such as triethylamine or N-methylmorpholine and chloroformic esters, with active esters via N-hydroxysuccinimide (HOSU) and dicyclohexylcarbodiimide (DCC) or by addition of EEDQ (1-ethoxycarbonyl-2-ethoxy-1,2-dihydroquinoline). Alcohol residues can be introduced, for example, by acid catalysis (HCl) or with water-eliminating reagents such as, for example, thionyl chloride or DCC; this is carried out in inert organic solvents such as, for example, tetrahydrofuran, dichloromethane, toluene or t-butyl methyl ether.

The radical B is eliminated in the case of BOC preferably with HCl or trifluoroacetic acid and in the case of CBZ preferably by hydrogenolysis.

The reaction of III with IV preferably takes place in the presence of an acid-binding agent such as, for example, triethylamine or sodium hydroxide solution. Examples of inert solvents which are employed are dichloromethane, toluene or t-butyl methyl ether.

In the reaction according to process variant B, the coupling of V with VI preferably takes place by activation with bases such as triethylamine or N-methylmorpholine and chloroformic ester, by preparing an active ester with HOSU and DCC, or by addition of EEDQ in an inert organic solvent such as, for example, tetrahydrofuran, dichloromethane or t-butyl methyl ether.

The invention also relates to the optically active polymers and copolymers which can be obtained by, respectively, polymerisation and copolymerisation of the optically active dipeptides of the formula (I) and which contain at least 40 mol %, preferably at least 50 mol %, of structural units of the formula (VII),

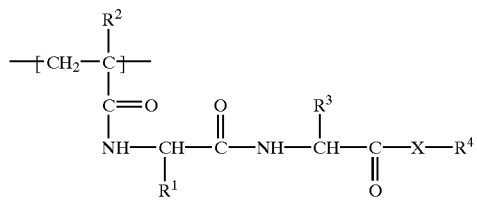

in which
R¹ to R⁴ and X have the meanings stated for formula (I).

The optically active polymers of the formula (VII) according to the invention are preferably in the form of crosslinked insoluble but swellable bead polymers or in a form bound to finely divided inorganic support materials such as, for example, silica gel. They can also be prepared as linear polymers which are soluble in suitable organic solvents. It is furthermore possible to copolymerise various dipeptides of the formula (I) according to the invention, as well as to incorporate 0.1 to 60, preferably 0.1 to 20, mol % of other copolymerisable monomers into the polymers.

The mechanical properties of the optically active bead polymers, especially the pressure stability in the swollen state, can be improved by incorporating 2 to 60% by weight (based on the monomer and crosslinker) of a finely divided inorganic filler.

Suitable as inorganic filler are insoluble, finely divided, crystalline or amorphous inorganic compounds with an average particle size from 3 nm to 10 μm, preferably 10 to 500 nm.

Examples of suitable fillers are hydroxides, oxides, carbonates, sulphates and phosphates of metals, such as aluminium hydroxide, aluminium oxide, aluminium oxide hydrate, titanium dioxide, zirconium dioxide, calcium carbonate, dolomite, calcium sulphate, barium sulphate, calcium phosphate and zirconium phosphate. Silicate fillers are preferred, such as, for example, kaolin, calcined kaolin, mica, wollastonite, calcium silicate, aluminium silicate, sodium aluminium silicate, zirconium silicate, powdered quartz and amorphous silicon dioxide, furthermore finely ground glasses and glass ceramics. Microfine silicon dioxide obtained by flame hydrolysis is particularly preferred and is obtainable as commercial product, for example, under the name Aerosil or HDS (highly disperse silica).

The magnitude of the specific surface area of the inorganic filler is important for the quality and the separation properties of the bead polymers according to the invention. The specific surface area should be 30 to 500 m²/g, preferably 50 to 400 m²/g, measured by the BET method (gas adsorption).

The inorganic fillers are preferably used in a form treated with adhesion promoters. Examples of suitable adhesion promoters are silane and titanium compounds, such as trimethylchlorosilane, hexamethylenedisiloxane, 3-aminopropyltrimethoxysilane, butyl titanate and isopropyl titanate. Particularly preferred adhesion promoters have polymerisable groups such as vinyltrimethoxysilane, vinyltriethoxysilane, vinylethyldiethoxysilane, allyltriethoxysilane, γ-methacryloxypropyltrimethoxysilane, γ-methacryloxypropyltriethoxysilane, γ-acryloxypropyltrimethoxysilane, γ-acryloxypropyltriethoxysilane, γ-methacryloxypropylmethyldiethoxysilane.

The crosslinked polymers are preferably in the form of small particles (beads) with a particle diameter of 5 to 200 μm. They are prepared, for example, by suspension polymerisation of the optically active dipeptides of the formula (I) with 0.5 to 50 mol %, preferably 1 to 30 mol %, particularly preferably 3 to 20 mol % (based on the total amount [mol] of the monomers employed) of a suitable crosslinker, in a manner known per se.

The degree of swelling of the (bead) polymers can be adjusted by the nature and amount of the crosslinkers and of the solvent by customary methods.

On practical use, (bead) polymers with a degree of swelling (S) of 1.1 to 12.0, preferably of 2.0 to 6.0, have proven suitable.

The degree of swelling S is determined as follows:

$$Q = \frac{\text{polymer volume (swollen)}}{\text{polymer volume (unswollen)}}$$

Suitable crosslinkers are compounds which contain at least two polymerisable vinyl groups. Preferred crosslinkers are alkanediol diacrylates such as 1,6-hexanediol diacrylate, 1,4-butanediol diacrylate, 1,3-propanediol diacrylate or 1,2-ethylene glycol diacrylate, or alkanediol dimethacrylates such as 1,4-, 1,3- or 2,3-butanediol dimethacrylate, 1,3-propanediol dimethacrylate or 1,2-ethyleneglycol dimethacrylate, aromatic divinyl compounds such as, for example, divinylbenzene, divinylchlorobenzene or divinyltoluene, divinyl dicarboxylates such as divinyl adipate, divinyl benzene-dicarboxylates, divinyl terephthalate, N,N'-alkylene-diacrylamides such as N,N'-methylenediacrylamide, N,N'-ethylenediacrylamide, N,N'-methylenedimethacrylamide, N,N'-ethylenedimethacrylamide or N,N'-dimethylethylenediacrylamide. It is likewise possible to use N,N',N"-tris(acryloyl)-1,3,5-perhydrotriazine or N,N'-bis(acryloyl)piperazine.

Suitable free-radical formers are the customary free-radical formers. Peroxides are preferred, such as, for example, dibenzoyl peroxide, dilauroyl peroxide or di-ortho-tolyl peroxide, peresters such as tert.-butyl perpivalate or tert.-butyl peroctanoate, or azo compounds such as, for example, azobisisobutyronitrile (AIBN). It is also possible to use mixtures of various free-radical formers.

The polymerisation components are dissolved in an organic solvent which is immiscible with water, preferably an aliphatic or aromatic hydrocarbon such as hexane, heptane, isodecane, benzene or toluene, a halogenated hydrocarbon, such as di-, tri-, tetrachloromethane or 1,2-dichloroethane, an ester such as ethyl acetate, butyl acetate or dialkyl carbonates or a ketone which is insoluble in water, such as methyl isobutyl ketone or cyclohexanone.

The organic phase is uniformly dispersed with the aid of an effective stirrer in the aqueous solution of a protective colloid, preferably in an aqueous solution of polyvinyl alcohol, polyvinylpyrrolidone or of a copolymer of methacrylic acid and methyl methacrylate. About 1 to 20, preferably 2 to 10, parts by weight of aqueous phase are employed per part by weight of organic phase. The polymerisation mixture is heated to temperatures from 30° C. to 100° C., preferably 40° C. to 80° C., while stirring in an inert gas atmosphere, preferably under nitrogen. The polymerisation time is between 2 and 24, preferably 4 and 12 hours. The copolymer obtained in this way is separated from the liquid phase by filtration, purified by thorough washing with water and with organic solvents such as methanol, ethanol, benzene, toluene, di-, trichloromethane or acetone and subsequently dried.

The optically active polymers according to the invention are, especially for analytical applications, preferably employed in a form bound to finely divided inorganic supports. Optically active chromatography phases of this type can be prepared, for example, by the processes described in DE-A 3,706,890.

The optically active dipeptides of the formula (I) are preferably polymerised in the presence of silica gel-vinyl phases which are obtainable by known methods, or of silica gel-methacrylate phases which can be obtained by esterification of silica gel-diol phases or by reaction of silica gel with γ-methacryloxypropyltrimethoxysilane. In this connection, polymerisation can be carried out in the absence of solvents or in the presence of solvents or of precipitants for the polymers of the dipeptides of the formula (I). The initiators which can be employed are likewise the free-radical formers used for preparing the bead polymers.

The polymer-modified silica gels preferably contain 1 to 40% by weight, in particular 3 to 30% by weight, of optically active monomer (I) based on the total weight. They are thoroughly washed with solvents for the polymer and are dried in vacuo.

It is, of course, also possible here to employ mixtures of two or more of the dipeptides according to the invention, where appropriate also with other copolymerisable monomers.

The invention furthermore relates to the use of the polymers of the formula (I) according to the invention as such or in a form which is crosslinked or bound to silica gel for the chromatographic separation of racemic mixtures into the optical antipodes. The polymers according to the invention have proved particularly suitable for the chromatographic separation of hexahydrocarbazole derivatives such as, for example, 3-r-(4-fluorophenylsulphonamido)-9-(2-carboxyethyl)-1,2,3,4,4a,9a-hexahydrocarbazole (Rac I), benzodiazepines such as, for example, oxazepam (Rac II), arylpropionic acids such as, for example, 2-(4-isobutylphenyl)propanoic acid (Rac III), 2-(3-benzoyl) propanoic acid (Rac IV), dihydropyridine derivatives, such as, for example, 1,4-dihydro-2,6-dimethyl-4-(2-trifluoromethylphenyl)pyridine-3,5-dicarboxylic acid 5-methyl ester (Rac V), 3-isopropyl 5-(2-methoxyethyl) 1,4-dihydro-2,6-dimethyl-4-(3-nitrophenyl)-3,5-dicarboxylate (Rac VI), chlorthalidone (Rac VII), biaryls such as, for example, 2,2'-dimethoxy-6,6'-dinitro-biphenyl (Rac VIII), cyclopropanecarboxylic acids such as, for example, cis-3-[2-chloro-4-(2-chlorophenyl)-ethenyl]-2,2-dimethylcyclopropanecarboxylic acid (Rac IX).

The composition of the eluent can be selected and optimised in a customary way depending on the nature and property of the racemate to be separated. The polymers according to the invention which are bound to silica gel can be employed for chromatographic separations of racemates under HPLC conditions.

The capacity of the polymers for separating racemates is expressed by the capacity ratios ($k'_{1(2)}$ values) for the two enantiomers (1) and (2) and the enantioselectivity value α resulting therefrom. These chromatographic parameters are defined as follows:

$$\text{capacity ratio } k'_{1(2)} = \frac{t_{1(2)} - t_o}{t_o}$$

$$\text{enantioselectivity } \alpha = \frac{k'_2}{k'_1}$$

$t_o$=dead time of the column $t_{1(2)}$=retention time of, respectively, enantiomer 1 which is eluted first and enantiomer 2 which is eluted later.

Preparative separation of racemic mixtures into their optical antipodes using the polymers according to the invention is preferably carried out by column chromatography. Particularly advantageous for this is to carry out the chromatographic separation with bead polymers with a defined particle size distribution; good separation efficiencies are obtained with bead polymers with a particle size distribution from 5 to 200 μm, preferably 15 to 100 μm.

The methods for carrying out separation by column chromatography are known. Normally, the polymer is suspended in eluent, and the suspension is packed into a glass column. After the eluent has run out, the racemate to be separated is loaded, dissolved in the eluent, onto the column. Elution is then carried out with the eluent, and the enantiomers in the eluate are detected by photometry and/or polarimetry with the aid of suitable flow cells.

Normally used as eluents are organic solvents or solvent mixtures which swell the polymer employed as adsorbent and dissolve the racemate which is to be separated. Examples which may be mentioned are: hydrocarbons such as benzene, toluene or xylene, ethers such as diethyl ether, tert.-butyl methyl ether, dioxane or tetrahydrofuran, halogenated hydrocarbons such as di- or trichloromethane, acetone, acetonitrile or ethyl acetate, alcohols such as methanol, ethanol, n-propanol, isopropanol or n-butanol, or else mixtures of the said solvents. Mixtures of toluene with tetrahydrofuran, dioxane or isopropanol have proved particularly suitable.

The surprisingly good separating properties of the separation phases according to the invention may be illustrated by a few examples. The separation phases are each prepared by the same process and employed in a form bound to silica gel.

Table 1 shows a comparison of the enantioselectivities α of separation phases with structurally identical "end group"; on the one hand those of an N-methacryloyl-S-Leu-S-Ile t-butyl ester phase A, according to the invention, and on the other hand those of an N-methacryloyl-S-Ile t-butyl ester phase B, which makes the difference according to the invention on changing from an amino acid phase B to a dipeptide phase A obvious.

TABLE 1

| Racemate | α on dipeptide phase A | α on amino acid phase B |
|---|---|---|
| Rac I | 16.70 | 3.11 |
| Rac II | 2.00 | <1.02 |
| Rac V | 1.35 | <1.02 |
| Rac VII | 2.20 | 1.16 |
| Rac VIII | 12.00 | 1.35 |
| Rac IX | 1.53 | <1.02 |

Table 2 shows a comparison of the enantioselectivities α of separation phases with structurally identical "head group"; on the one hand those of an N-methacryloyl-S-Nle-S-Ile t-butyl ester phase C according to the invention, and on the other hand those of an N-methacryloyl-S-Nle d-menthylamide phase D, from which the surprising difference between a dipeptide phase C according to the invention and a "simple" amino acid phase D is likewise evident.

TABLE 2

| Racemate | α on dipeptide phase C | α on amino acid phase D |
|---|---|---|
| Rac III | 1.16 | <1.02 |
| Rac IV | 1.10 | <1.02 |
| Rac VI | 1.10 | <1.02 |
| Rac VIII | 8.75 | 3.20 |
| Rac IX | 1.45 | <1.02 |

EXEMPLARY EMBODIMENTS

Route A: N-BOC-amino acid precursors

EXAMPLE 1

N-methacryloyl-S-Val-S-Ala 1-bornyl ester 21.7 g of N-BOC-S-Val were added to 250 ml of tetrahydrofuran, followed by dropwise addition of 10.1 g of triethylamine at 0° C. and of 10.9 g of ethylchloroformate at −13° C. After 10 minutes at this temperature, 22.5 g of S-Ala 1-bornyl ester in 75 ml of tetrahydrofuran were added dropwise. The mixture was allowed to warm up and was evaporated in a rotary evaporator, the residue was taken up in dichloromethane and the solution was washed with water, 1 N HCl and half-saturated sodium bicarbonate solution and was dried over magnesium sulphate. It was evaporated to 100 ml in a rotary evaporator and, at 0° C., 100 ml of trifluoroacetic acid were added and the mixture was stirred at room temperature for 2 hours. It was concentrated, taken up in dichloromethane and, while cooling in ice, adjusted to pH 11–12 with 20% strength sodium hydroxide solution. Then extraction took place 2× with dichloromethane, and drying over magnesium sulphate and concentration to a volume of 275 ml were carried out. At 0° C., 11.1 g of N-methylmorpholine and 9.6 g of methacryloyl chloride in 50 ml of dichloromethane were added, the mixture was stirred at room temperature for 1 hour, washed with water, 1 N HCl and half-saturated sodium bicarbonate solution, and the organic extracts were dried over MgSO$_4$. The resulting crude product (31.6 g) was purified by chromatography on silica gel with t-butyl methyl ether/petroleum ether, and 19.5 g of product of melting point 35° C. were obtained.

EXAMPLE 2

N-methacryloyl-S-Val-S-Val t-butylamide 2 g of S-Val t-butylamide and 2 g of N-methylmorpholine in 200 ml of diethyl ether were added dropwise to a solution of 3.14 g of N-BOC-S-Val hydroxysuccinimide ester in 250 ml of the same solvent. The mixture was stirred overnight, washed 2× with water, dried over magnesium sulphate and evaporated to dryness in vacuo. Crystallisation from t-butyl methyl ether/petroleum ether resulted in 3 g of product of melting point 230° C.

Route B: N-(meth)acryloylamino acid precursors

EXAMPLE 3

N-methacryloyl-S-Ala-S-Ala 1-bornyl ester 22.5 g of S-Ala 1-bornyl ester in 250 ml of dichloromethane, and then 27.2 g of 1-ethoxycarbonyl-2- ethoxy-1,2-dihydroquinoline (EEDQ) in 125 ml of dichloromethane, were added dropwise at 0° C. to a solution of 15.7 g of N-methacryloyl-S-Ala in 100 ml of dichloromethane. The mixture was stirred at room temperature for 3 days, washed 5× with 1 N HCl, dried over magnesium sulphate and evaporated to dryness. Crystallisation of the crude product (37 g) from heptane resulted in 20.6 g of title compound of melting point 60–62° C.

EXAMPLE 4

N-acryloyl-S-Phe-S-Phe isopropyl ester

First 20.7 g of S-Phe isopropyl ester in 50 ml of tetrahydrofuran, and then a solution of 27.3 g of EEDQ in 100 ml of abs. THF, were added dropwise at 0° C. to 21.9 g of N-acryloyl-S-phenylalanine in 400 ml of tetrahydrofuran. The mixture was stirred at room temperature for 3 days and evaporated to dryness, and the residue was taken up in dichloromethane. The solution was washed 5× with 1 N HCl, dried over magnesium sulphate and evaporated in a rotary evaporator. 54 g of crude product and, after crystallisation from toluene/petroleum ether, 33.7 g of product of melting point 134° C. were obtained.

EXAMPLE 5

N-Methacryloyl-S-Leu-S-Phe d-menthyl ester 30.3 g of S-Phe d-menthyl ester in 100 ml of ethyl acetate, and then 27.2 g of EEDQ in 100 ml of the same solvent, were added dropwise at 0° C. to a solution of 19.9 g of N-methacryloyl-S-Leu in 200 ml of ethyl acetate. The mixture was stirred at room temperature for 3 days and worked up as described above. Purification of the crude product by chromatography on silica gel with t-butyl methyl ether/petroleum ether resulted in 20.2 g of title compound of melting point 38° C.

TABLE 3

Monomeric dipeptides of the formula (I)

$$R^1-\underset{\underset{\underset{R^2}{|}}{\underset{C=CH_2}{|}}}{\underset{CO}{\underset{|}{\underset{NH}{\underset{|}{CH}}}}}-\overset{O}{\overset{||}{C}}-NH-\underset{\underset{}{}}{\overset{R^3}{\overset{|}{CH}}}-\overset{}{\underset{\underset{}{O}}{\overset{||}{C}}}-X-R^4 \quad (1)$$

| Ex. No. | $R^1$ | $R^2$ | $R^3$ | X | $R^4$ | m.p. (° C.) | Rotation $\alpha_D$ (C = 1, CHCl$_3$) | Name |
|---|---|---|---|---|---|---|---|---|
| 6 | $CH_3$ | $CH_3$ | $CH_2SCH_3$ | NEt | Et | 110 | −53.7 | N-MA*-S-Ala-R-(S)-methyl-Cys diethylamide |
| 7 | $CH_3$ | $CH_3$ | $(CH_2)_2SCH_3$ | NH | 3-pentyl | 177–179 | −54.9 | N-MA-S-Ala-S-Met 3-pentylamide |
| 8 | $CH_3$ | $CH_3$ | iPr | O | t-butyl | 105 | | N-MA-S-Ala-S-Val t-butyl ester |
| 9 | $CH_3$ | $CH_3$ | sBu | O | t-butyl | 60–65 | −13.0 | N-MA-S-Ala-S-Ile t-butyl ester |
| 10 | Ph | $CH_3$ | iPr | O | t-butyl | 156 | +73.3° | N-MA-S-Phg-S-Val t-butyl ester |
| 11 | $CH_3$ | $CH_3$ | iBu | O | d-menthyl | 155 | | N-MA*-S-Ala-S-Leu d-menthyl ester |
| 12 | $CH_3$ | $CH_3$ | $CH_2Ph$ | O | d-menthyl | oil | | N-MA-S-Ala-S-Phe d-menthyl ester |
| 13 | nBu | $CH_3$ | sBu | O | t-butyl | 136 | −9.3 | N-MA-Nle-S-Ile t-butyl ester |
| 14 | iBu | $CH_3$ | $CH_2Ph$ | O | l-menthyl | 104 | | N-MA-S-Leu-R-Phe l-menthyl ester |
| 15 | iBu | $CH_3$ | sBu | O | t-butyl | 174 | −97.7 | N-MA-S-Leu-S-Ile t-butyl ester |
| 16 | i-Bu | $CH_3$ | iBu | O | d-menthyl | oil | | N-MA-S-Leu-S-Leu d-menthyl ester |
| 17 | $(CH_2)_2SCH_3$ | $CH_3$ | $CH_2Ph$ | O | d-menthyl | 103 | +25.2 | N-MA-S-Met-S-Phe d-menthyl ester |
| 18 | Ph | $CH_3$ | iPr | O | t-butyl | 123–124 | −52.2 | N-MA-R-Phg-S-Val t-butyl ester |
| 19 | iBu | $CH_3$ | sBu | O | 3-pentyl | 132 | −31.6 | N-MA-S-Leu-S-Ile 3-pentyl ester |
| 20 | Ph | $CH_3$ | $(CH_2)_2SCH_3$ | NEt | Et | 167 | +51.9 | N-MA-S-Phg-S-Met diethylamide |
| 21 | iBu | $CH_3$ | cyclohexyl | NEt | Et | 99 | −10.8 | N-MA-S-Leu-R-hexa-hydrophenylglycine diethylamide |

*MA = methacryloyl
A = acryloyl

Polymerisation of the Optically Active Dipeptides of the Formula I on Silica Gel a) Preparation of Vinyl-silica With strict exclusion of moisture, 50 g of silica gel (LiChrosorb Si 100, 5μ, Merck; Polygosil 100–5, Macherey & Nagel) dried at 120° C. are mixed with 600 ml of dry toluene. 100 ml of toluene are distilled out under $N_2$ and under atmospheric pressure.

After cooling to 30° C., 35 g of trichlorovinylsilane are added. The mixture is heated to reflux with stirring. Then 62 g of triethylamine in 150 ml of toluene are added dropwise over the course of 1 hour. The mixture is left to stir further at 105–108° C. overnight.

After cooling and filtration with suction on a glass frit, the silica gel is stirred successively in toluene, dichloromethane, methanol, methanol/water=60/40, methanol twice and dichloromethane twice, sucking thoroughly dry between each, and is finally dried at 70° C.

Analyses: C 2.8–3.2%; H 0.7–0.9% b) Preparation of the Compounds of the Formula VII in a Form Bound to Silica Gel

EXAMPLE 20

3.0 g of vinyl-silica, 2.0 g of monomer (see Table 4) and 40 mg of azobisisobutyronitrile are dissolved or suspended in 8 ml of toluene, toluene/heptane mixtures or chloroform. The apparatus is, with magnetic stirring, evacuated and flushed with nitrogen three times. The mixture is stirred at room temperature for 1 hour, then rapidly heated to 80° C. (or 65° C. for chloroform) and left at this temperature for 1 hour or 4 hours for chloroform mixtures. Addition of 100 mg of 2,6-di-tert.-butyl-4-methylphenol is followed by rapid cooling to room temperature. The silica gel is filtered off with suction through a G4 frit, stirred twice in chloroform, once in toluene and once in isopropanol for 15 min each, sucked thoroughly dry and dried at room temperature in vacuo (<0.005 atm).

Yield: 3.35 g±10%

See Table 4 for degree of loading.

TABLE 4

Silica gel phases

| Example No. | Monomer No./g | Solvent | N content [%] | Bound polymer [% by wt] |
|---|---|---|---|---|
| 21 | 17 2.0 | toluene | 1.1 | 19.8 |
| 22 | 7 1.0 | CHCl₃ | 1.3 | 11.1 |
| 23 | 6 1.0 | toluene | 2.8 | 22.0 |
| 24 | 19 2.0 | toluene | 1.15 | 15.7 |
| 25 | 4 2.0 | CHCl₃ | 0.7 | 10.2 |
| 26 | 5 1.5 | toluene | 0.6 | 10.4 |
| 27 | 12 2.0 | toluene | 1.05 | 16.6 |
| 28 | 14 2.0 | toluene | 0.75 | 13.0 |
| 29 | 15 2.0 | toluene | 1.35 | 17.8 |
| 30 | 2 2.0 | CHCl₃ | 1.2 | 9.7 |
| 31 | 3 2.0 | toluene | 1.5 | 19.6 |
| 32 | 13 2.0 | toluene | 0.9 | 11.9 |
| 33 | 16 2.0 | toluene | 0.75 | 12.1 | c) Polmerisation of the Optically Active Dipeptides of the Formula I to Give Bead Polymers of Formula VII

EXAMPLE 34

13.0 g of N-methacryloyl-S-Ala-S-Leu d-menthyl ester (compare Monomer Example 12)), 2.0 g of ethylene glycol dimethacrylate (EGDMA), 0.5 g of azobisisobutyronitrile, 37.5 g of trichloromethane and a solution of 4 g of polyvinyl alcohol in 130 ml of 1M phosphate buffer pH 6.0 are introduced into a 250 ml stirring apparatus. The apparatus is evacuated and refilled with nitrogen several times. The mixture is then stirred at 425 rpm under nitrogen and polymerised at 50° C. for 15 min and at 55° C. for 14 hours. The very fine fractions <10 μm are removed by repeated sedimentation in water, and the beads are filtered off with suction, washed thoroughly with acetone, trichloromethane and acetone again, and dried at 50° C.

Yield: 12.3 g of bead polymer

Particle size: 15–50 μm

Apparent volume: 1.9 ml/g

Swollen volume: 5.4 ml/g (in toluene/THF=3/2 (V/V))

What is claimed is:

1. Polymerisable enantiomers of optically active dipeptides of the general formula (I)

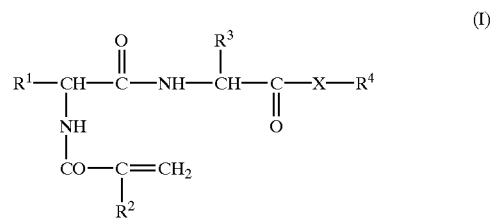

in which $R^1$ and $R^3$ are identical or different and represent $C_1$–$C_5$-alkyl, A—O—$CH_2$, A—S—$CH_2$, $CH_3$—S—$(CH_2)_2$, cyclohexyl-$CH_2$, cyclohexyl, phenyl, benzyl, 4-A—O-benzyl, benzyl-$CH_2$, indolyl, naphthyl-$CH_2$ or naphthyl, where A is hydrogen, methyl, t-butyl or benzyl, $R^2$ denotes hydrogen, methyl or fluorine, X represents oxygen or $NR^5$, wherein $R^5$ is hydrogen, methyl, ethyl or, together with $R^4$, forms a $C_5$–$C_6$-cycloalkyl radical, and $R^4$ represents a straight-chain or branched $C_3$–$C_{18}$-alkyl radical or a mono- to tetra-$C_1$–$C_4$-alkyl-substituted $C_3$–$C_{12}$-cycloalkyl radical, benzyl, 1-phenyl-ethyl or represents a phenyl which is mono- to disubstituted by fluorine, chlorine, trifluoromethyl, methoxy or $C_1$–$C_4$-alkyl.

2. Polymerisable optically active dipeptides according to claim 1, where $R^1$, $R^3$ and $R^5$ have the meaning stated in claim 1, $R^2$ denotes hydrogen or methyl, and $R^4$ represents $C_3$–$C_8$-alkyl, $C_5$–$C_7$-cycloalkyl, up to tetra-$C_1$–$C_4$-alkyl-substituted $C_6$-cycloalkyl, benzyl, 1-phenylethyl, phenyl, 4-t-butylphenyl, 3,5-dichlorophenyl or 3,5-dimethylphenyl.

3. Polymerisable optically active dipeptides according to claim 1, which are derived from the amino acids alanine, amino butyric acid, valine, norvaline, leucine, isoleucine, terleucine, norleucine, neopentylglycine, serine, cysteine, methionine, hexahydrophenylalanine, hexahydrophenylglycine, phenylglycine, phenylalanine, tyrosine, homophenylalanine, tryptophan, naphthylalanine or naphthylglycine.

4. Polymerisable optically active dipeptides according to claim 1, where the dipeptides are N-methacryloyl-S-Leu-S-Ile O-t-butyl ester,
N-methacryloyl-S-Leu-S-Phe d-menthyl ester,
N-methacryloyl-S-Leu-S-Leu 3-pentylamide, N-methacryloyl-S-Val-S-Val t-butylamide, N-acryloyl-S-Phe-S-Phe 2-propyl ester, N-methacryloyl-S-Val-S-Ala 1-bornyl ester, N-methacryloyl-S-Ala-S-Met 3-pentylamide, N-methacryloyl-R-Phg-S-Val t-butyl ester, N-methacryloyl-S-Leu-R-Phe l-menthyl ester, N-methacryloyl-S-Ala-R-(S)-methyl-Cys diethylamide, N-methacryloyl-S-Ala-S-Leu d-menthyl ester.

5. Polymerisable optically active dipeptides according to claim 1, wherein $R^4$ is a member selected from the group consisting of 2-propyl, 3-pentyl, t-butyl, neopentyl, $C_5$–$C_7$-cycloalkyl, $C_6$-cycloalkyl substituted up to four times by $C_1$–$C_4$-alkyl, benzyl, 1-phenylethyl, phenyl, 4-t-butylphenyl, 3,5-dichlorophenyl and 3,5-dimethylphenyl.

6. Polymerisable optically active dipeptides according to claim 1, wherein $R^4$ is member selected from the group consisting of 2-propyl, 3-pentyl, t-butyl, neopentyl, cyclopentyl, cyclohexyl, cycloheptyl, methyl, bornyl, fenchyl, benzyl, 1-phenylethyl, phenyl, 4-t-butylphenyl, 3,5-dichlorophenyl and 3,5-dimethylphenyl.

* * * * *